(12) United States Patent
Mitchell

(10) Patent No.: US 9,237,961 B2
(45) Date of Patent: Jan. 19, 2016

(54) STENT DELIVERY SYSTEM FOR DETECTING WALL APPOSITION OF THE STENT DURING DEPLOYMENT

(75) Inventor: James Mitchell, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1041 days.

(21) Appl. No.: 12/766,067

(22) Filed: Apr. 23, 2010

(65) Prior Publication Data

US 2011/0263960 A1 Oct. 27, 2011

(51) Int. Cl.
A61F 2/06 (2013.01)
A61F 2/958 (2013.01)

(52) U.S. Cl.
CPC ......... *A61F 2/958* (2013.01); *A61F 2250/0001* (2013.01); *A61F 2250/0096* (2013.01)

(58) Field of Classification Search
CPC ........... A61B 2018/00875; A61B 2018/00892; A61B 2018/00898; A61B 2018/00904; A61B 2019/465; A61B 5/04; A61B 5/6853; A61B 5/0488; A61F 2/958; A61F 2250/0043; A61F 2/95–2/97; A61F 2250/0001; A61F 2250/0096
USPC .............. 623/1.11, 1.15, 1.23, 1.34; 600/373, 600/393; 606/108, 130
See application file for complete search history.

(56) References Cited

U.S. PATENT DOCUMENTS

| 5,158,537 | A | * | 10/1992 | Haak et al. ...................... 604/20 |
| 5,341,807 | A | * | 8/1994 | Nardella ........................ 600/381 |
| 5,665,103 | A | * | 9/1997 | Lafontaine et al. ............ 606/192 |
| 5,668,170 | A | * | 9/1997 | Gyory ............................ 514/449 |
| 5,800,443 | A | | 9/1998 | Shah |
| 5,928,248 | A | | 7/1999 | Acker |
| 6,053,873 | A | * | 4/2000 | Govari ................. A61B 5/0031 600/462 |
| 6,091,980 | A | * | 7/2000 | Squire et al. ................... 600/381 |
| 6,095,987 | A | | 8/2000 | Shmulewitz et al. |
| 6,179,858 | B1 | * | 1/2001 | Squire ..................... A61F 2/958 606/159 |
| 6,304,776 | B1 | * | 10/2001 | Muntermann ................. 600/547 |
| 6,477,410 | B1 | * | 11/2002 | Henley et al. ................... 604/20 |

(Continued)

FOREIGN PATENT DOCUMENTS

| EP | 0882430 | 12/1998 |
| WO | WO97/45157 | 12/1997 |
| WO | WO2006/127997 | 11/2006 |

OTHER PUBLICATIONS

International Search Report and Written Opinion of the ISA re: International application No. PCT/US2011/029546, dated Jul. 6, 2011.

*Primary Examiner* — David C Eastwood
*Assistant Examiner* — Erin Colello

(57) ABSTRACT

A stent delivery and apposition detecting system includes at least one electrode pair of dissimilar metals mounted on a balloon of a balloon catheter. The electrode pair forms part of an electrochemical cell, and voltage and current generated from the electrochemical cell enables the system to detect when a stent mounted on the balloon achieves proper wall apposition. As the balloon is exposed to different environments, i.e., blood or tissue having different resistances, the electric potential of the electrochemical cell changes and an alert is generated by a feedback circuit to notify a user that the electrodes are in contact with tissue of the vessel wall. In one embodiment, the feedback circuit may be powered by the electrochemical cell. Multiple sets of electrode pairs may be mounted along the circumference and length of the balloon to detect differential contact between the deployed stent and the vessel wall.

23 Claims, 3 Drawing Sheets

(56) References Cited

U.S. PATENT DOCUMENTS

| | | | |
|---|---|---|---|
| 6,546,270 B1* | 4/2003 | Goldin et al. | 600/374 |
| 2002/0046756 A1* | 4/2002 | Laizzo et al. | 128/899 |
| 2002/0065530 A1* | 5/2002 | Mische | A61M 25/10 606/151 |
| 2004/0230131 A1* | 11/2004 | Kassab | A61B 5/053 600/547 |
| 2005/0033281 A1* | 2/2005 | Bowman et al. | 606/41 |
| 2008/0146894 A1* | 6/2008 | Bulkes et al. | 600/300 |
| 2008/0215117 A1* | 9/2008 | Gross | A61F 2/82 607/59 |
| 2009/0192405 A1* | 7/2009 | Carney | A61B 17/320758 600/547 |
| 2009/0247933 A1* | 10/2009 | Maor et al. | 604/20 |
| 2010/0010612 A1* | 1/2010 | Gelbart et al. | 623/1.11 |

* cited by examiner

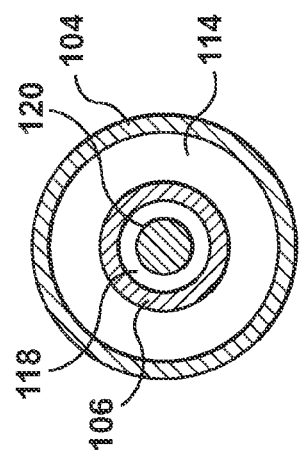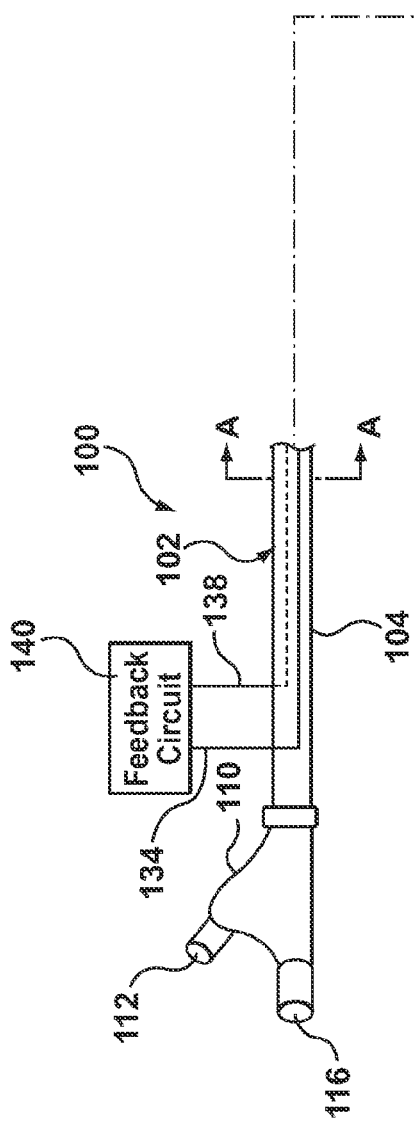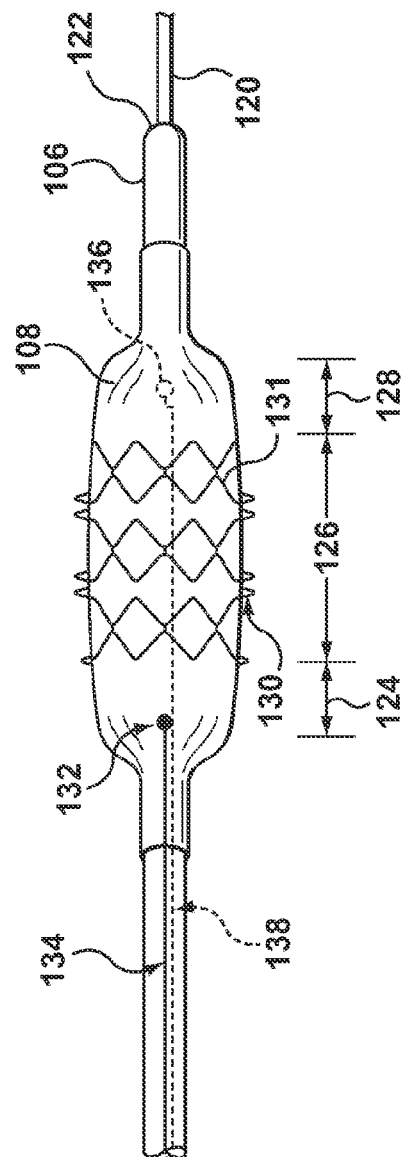

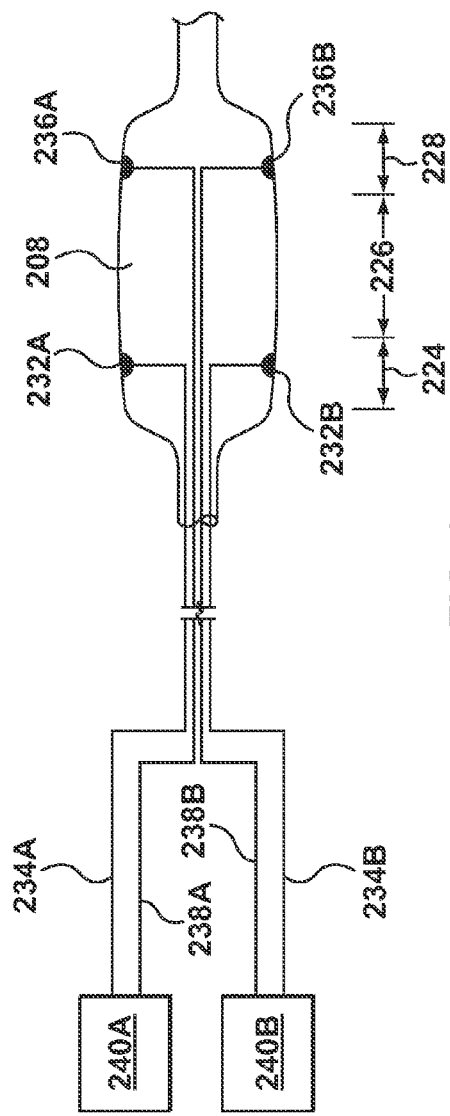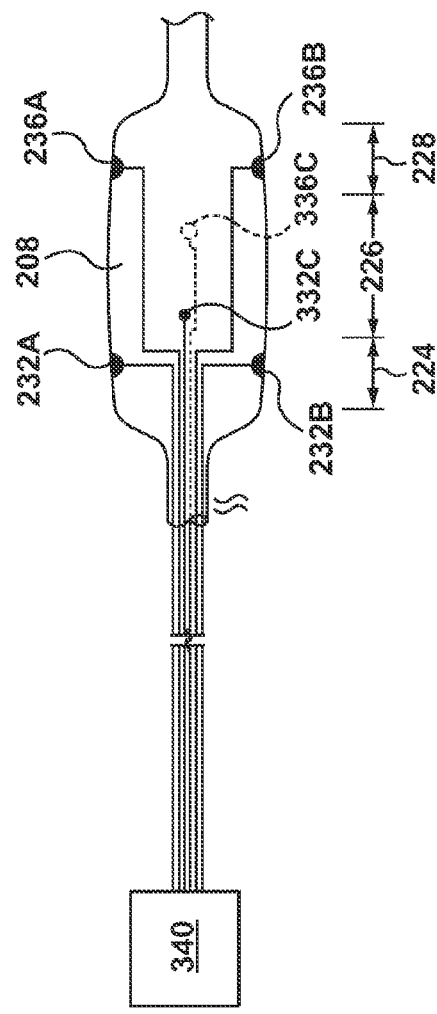

STENT DELIVERY SYSTEM FOR DETECTING WALL APPOSITION OF THE STENT DURING DEPLOYMENT

FIELD OF THE INVENTION

The invention relates to a stent delivery system that detects when a balloon expandable stent achieves wall apposition during deployment.

BACKGROUND OF THE INVENTION

Stent prostheses are known for implantation within body lumens to provide artificial radial support to a collapsing, weakened, and/or occluded passageway, such as blood vessels of the body. Stent prostheses are typically constructed of a metal or polymer and are generally a hollow cylindrical shape. When a balloon-expandable stent is to be implanted, a balloon catheter carrying the stent mounted on its balloon is advanced to the target site, such as a stenosis. The balloon and accompanying stent are positioned at the location of the stenosis, and the balloon is inflated to circumferentially expand and thereby implant the stent. As the balloon expands, it physically forces the stent to radially expand such that the outside surface of the stent comes into contact with the vessel wall. Thereafter, the balloon is deflated and the balloon catheter is withdrawn from the patient, leaving the stent in the expanded or deployed configuration.

One criterion for successful stent deployment is apposition of the stent against the vessel wall, since any regions of the stent that protrude into the lumen may cause blood turbulence, which in turn may lead to acute thrombosis and arterial blockage. By "apposition" or "wall apposition" herein it is meant that at least the outer surface of the deployed stent is fully positioned against, i.e., makes contact with, the vessel wall. The desire to prevent incomplete apposition leads to the common practice of dilating the stent after it is initially expanded with a second high-pressure balloon. This procedure intentionally overexpands the stent to ensure full apposition but may cause unnecessary injury to the vessel, which may lead to the primary failure mode of stents: the chronic hyperproliferative growth of smooth muscle cells called neointimal hyperplasia. This growth impinges on the lumen and reduces blood flow, which in approximately 30% of all stented patients is severe enough to require further intervention within three months of stent implantation.

In addition, the geometry or shape of many vessel lesions compounds the problem of incomplete vessel apposition. A so-called focal lesion is one that has a generally thicker midsection with one or more tapered ends, with the thicker midsection resulting in a constricted or occluded body lumen. When a stent is expanded over a focal lesion, the proximal and distal ends of the stent may not be apposed to the vessel wall although the middle of the stent has expanded sufficiently to restore patency. In order to achieve full apposition, the proximal and distal ends of the stent may require further expansion relative to the middle of the stent.

There exists a need in the art to ensure that a balloon expandable stent achieves complete or full apposition against the vessel wall during deployment. It is an object hereof to provide a stent delivery system that enables a physician the ability to adequately deploy a stent such that the implant will have complete apposition against the vessel wall.

BRIEF SUMMARY OF THE INVENTION

Embodiments hereof relate to a stent delivery system that alerts a user when a balloon expandable stent achieves complete vessel wall apposition during deployment, i.e., when at least the outer surface of the deployed stent is fully positioned against or makes contact with the vessel wall. The stent delivery and apposition detecting system includes a balloon catheter having a balloon mounted at the distal end thereof and at least one electrode pair of dissimilar metals mounted on the balloon. The stent delivery and apposition detecting system uses the electric potential of an electrochemical cell created by the electrode pair to detect when the stent achieves proper vessel wall apposition during deployment. The stent delivery system includes a feedback circuit that generates an alert when the electric potential of the electrochemical cell indicates that the electrode pair is in contact with tissue of the vessel wall. In one embodiment, the feedback circuit is powered by the electrochemical cell.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side schematic illustration of a stent delivery and apposition detecting system in accordance with an embodiment hereof, wherein the balloon is in an inflated configuration.

FIG. 1A is a cross-sectional view taken along line A-A of FIG. 1.

FIG. 2 is a side schematic illustration of a portion of a stent delivery and apposition detecting system having two sets of electrode pairs mounted on the balloon in accordance with another embodiment hereof, wherein the balloon is in an inflated configuration and the stent is removed from the balloon for clarity.

FIG. 3 is a side schematic illustration of a portion of a stent delivery and apposition detecting system having three sets of electrode pairs mounted on the balloon in accordance with another embodiment hereof, wherein the balloon is in an inflated configuration and the stent is removed from the balloon for clarity.

DETAILED DESCRIPTION OF THE INVENTION

Figure 4:
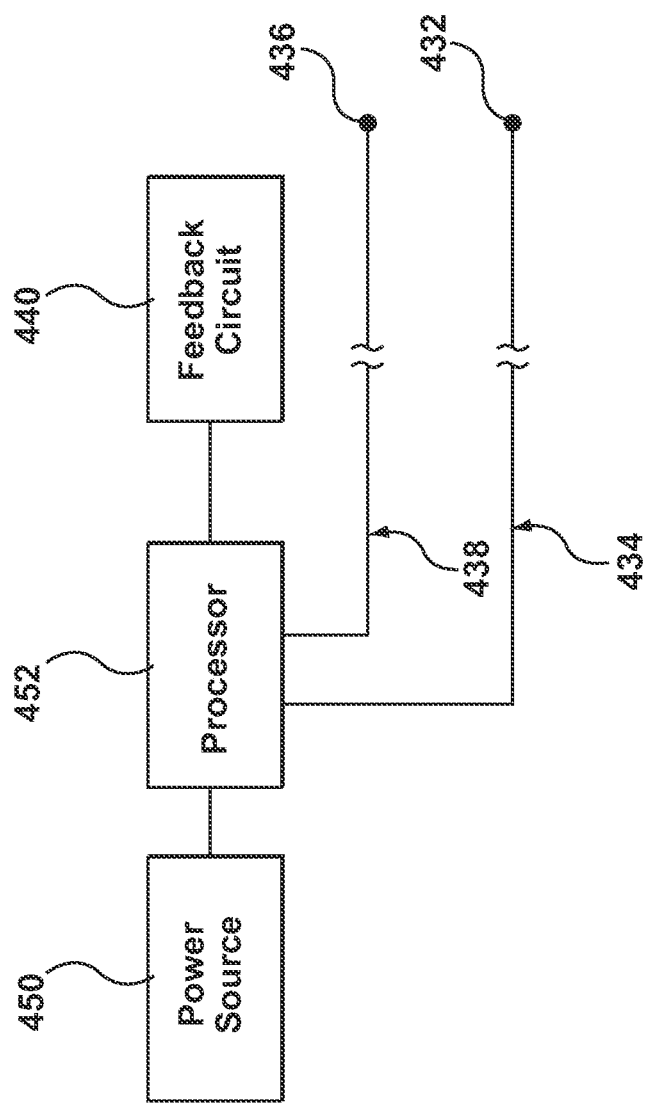
FIG. 4 is a schematic illustration of a circuit for use in a stent delivery and apposition detecting system in accordance with another embodiment hereof.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

FIGS. 1 and 1A depict a stent delivery and apposition detecting system 100 for tracking and deploying a stent 130 to a treatment site according to an embodiment hereof. Stent delivery and apposition detecting system 100 includes a balloon catheter 102 having a tubular component or outer shaft 104, an inner guidewire shaft 106, and an inflatable balloon 108 positionable at a target location within the vasculature. Balloon 108 is shown in an expanded or inflated configuration in FIG. 1. Outer shaft 104 has a proximal end that extends out of the patient and is coupled to a hub 110, and a distal end coupled to a proximal end of balloon 108. Guidewire shaft 106 is attached to hub 110 and terminates distally of balloon 108, defining a distal guidewire port 122. In the coaxial catheter construction of the illustrated embodiment, guidewire shaft 106 extends within outer shaft 104 such that an annular inflation lumen 114 is defined between an inner surface of outer shaft 104 and an outer surface of guidewire shaft 106. Other types of catheter construction are also amendable to the invention, such as, without limitation thereto, a catheter shaft formed by multi-lumen profile extrusion. Inflation lumen 114 allows inflation fluid received through an inflation port 112 of hub 110 to be delivered to balloon 108. As would be understood by one of ordinary skill in the art of balloon catheter design, hub 110 provides a luer hub or other type of fitting that may be connected to a source of inflation fluid and may be of another construction or configuration without departing from the scope of the present invention. In addition, hub 110 includes a guidewire port 116 that communicates with a guidewire lumen 118 of guidewire shaft 106 for receiving a guidewire 120 therethrough.

Stent 130 is crimped onto balloon 108 for delivery to the treatment site and expanded by the radial force of balloon 108. Balloon-expandable stent 130 may have any suitable configuration known in the art such as the balloon-expandable stents, for e.g., shown or described in U.S. Pat. No. 5,292,331 to Boneau, U.S. Pat. No. 6,090,127 to Globerman, and U.S. Pat. No. 5,133,732 to Wiktor, each of which is incorporated by reference herein in its entirety. For example, as shown in FIG. 1, stent 130 may have a cylindrically-shaped tubular body formed by a plurality of adjacent connected stent struts 131. One of ordinary skill in the art will appreciate that stent 130 can have any number of stent struts 131 depending upon the desired length of stent 130. In one embodiment, stent 130 is formed from a single helically wound elongate member having a continuous sinusoidal configuration. If desired, a sheath (not shown) may be provided to surround stent 130 to facilitate tracking of stent delivery and apposition detecting system 100 over guidewire 120 through the vasculature to a site of a stenotic lesion. Deployment of balloon expandable stent 130 is accomplished by advancing catheter 102 through the vascular system of the patient until stent 130 is located within target tissue, for example, a lesion which may include plaque obstructing the flow of blood through the vessel. Once positioned, a source of inflation fluid is connected to inflation port 112 of hub 110 so that balloon 108 may be inflated to radially expand stent 130 as is known to one of ordinary skill in the art. Stent deployment can be performed following treatments such as angioplasty, or during initial balloon dilation of the treatment site, which is referred to as primary stenting.

Balloon 108 of catheter 102 is inflated to such an extent that at least the outer surface of stent 130 is expanded or deployed into apposition with the vascular wall of the vessel, i.e., fully positioned against or makes contact with the vessel wall. Balloon 108 has mounted thereon at least one electrode pair of dissimilar metals, a first electrode 132 and a second electrode 136, that form part of an electrochemical or galvanic cell. In one embodiment, first electrode 132 is an anode or the electrode of the electrochemical cell at which oxidation occurs and second electrode 136 is a cathode or the electrode of the electrochemical cell at which reduction occurs. As will be understood by those of ordinary skill in the art, first electrode 132 may alternatively be the cathode and second electrode 136 may alternatively be the anode. The stent delivery and apposition detecting system 100 utilizes electric potential or voltage of the electrochemical cell to detect when stent 130 achieves proper wall apposition during deployment.

More particularly, two half-cells forming the electrochemical cell each include an electrode, i.e., first electrode 132 or second electrode 136, and an electrolyte from the environment surrounding balloon 108, i.e., blood or tissue. Electrochemical cells use oxidation-reduction chemical reactions to generate an electric current. More specifically, the current is caused through the transfer of electrons, i.e., releasing and accepting electrons, taking place between electrodes 132, 136. In the electrochemical cell, the difference between individual potentials of first and second electrodes 132, 136 with respect to the electrolyte is the cell potential or voltage. The cell potential of the electrochemical cell drives or transmits the current generated through the transfer of electrons along the length of balloon catheter 102 to a feedback circuit 140. As balloon 108 is exposed to different environments, i.e., as balloon 108 is advanced through blood and then inflated to abut tissue of the vessel wall, the electrolyte of the electrochemical cell changes. Since blood and tissue have different chemical properties, the electrochemical potential or voltage of the electrochemical cell will vary between blood and tissue for a given pairing of electrodes. An alert is generated by feedback circuit 140 when the voltage generated by the electrochemical cell indicates that first and second electrodes 132, 136 are in contact with tissue of the vessel wall. As such, stent delivery and apposition detecting system 100 alerts the user when stent 130 achieves proper wall apposition during deployment.

In one embodiment, first and second electrodes 132, 136 are longitudinally and circumferentially spaced apart from each other along/around balloon 108. First and second electrodes 132, 136 are relatively flat pieces of conductive material. Although depicted with a circular configuration, any geometrical configuration may be utilized. In an embodiment, first and second electrodes 132, 136 may be slightly thicker than stent 130 such that they come into contact with the vessel wall just prior to stent 130. As shown in FIG. 1, electrode 132 is mounted onto a proximal portion 124 of balloon 108 and electrode 136 is mounted onto a distal portion 128 of balloon 108, on the opposing side of balloon 108 from electrode 132. Balloon proximal portion 124 extends generally between a distal end of a proximal tapered portion of balloon 108 and a proximal end of stent 130 and balloon distal portion 128 extends generally between a distal end of stent 130 and a distal end of a distal tapered portion of balloon 108. First and second electrodes 132, 136 are thus spaced approximately one hundred eighty degrees apart such that the electrodes are positioned at two opposing locations around the circumference of balloon 108. The location of first and second electrodes 132, 136 spans the working length of balloon 108, i.e., the material of balloon 108 that comes into contact with the vessel wall when balloon 108 is inflated, to most accurately detect when the entire length and circumference of balloon 108 is in contact with tissue. Detecting that both proximal portion 124 and distal portion 128 of balloon 108 are pressed against the vessel wall is an indication that stent 130, mounted on an intermediate portion 126 of balloon 108, has been fully deployed and pressed against the vessel wall. In addition, the location of first and second electrodes 132, 136 at both proximal portion 124 and distal portion 128 of balloon 108 assists stent delivery and apposition detecting system 100 when stent 130 is deployed over a focal lesion. As described above, stent expansion over a focal lesion may require that the proximal and distal ends of a stent be further expanded than the intermediate portion of the stent in order to achieve full apposition against the vessel wall. The placement of first and second electrodes 132, 136 at proximal and distal portions 124, 128 of balloon 108 thus ensures that the proximal and distal ends of stent 130 are apposed against the vessel wall when the stent 130 is expanded over a focal lesion.

First and second electrodes 132, 136 are formed from dissimilar, biocompatible metals. Depending on the material thereof, each electrode 132, 136 has a characteristic or standard electrode potential. The standard electrode potential is a measure of potential for an individual electrode for a standard set of conditions or environment. The value of the standard electrode potential relates to the direction the electrode will react, either reducing or oxidizing, for that environment. Unique material pairings of first and second electrodes 132, 136 will result in different, predictable cell potentials. In one embodiment, the materials for the electrode pairing are metals that are far apart on the galvanic series. Otherwise stated, a most/more noble and non-active material such as platinum or gold is selected for the cathode and a least/less noble and active material such as magnesium or zinc is selected for the anode. A galvanic series is similar to the standard electrode potential however the electrode potentials are measured in a different environment that is more useful to a specific application. As an example, the galvanic series for materials are commonly reported in sea water or saline solutions as a large amount of corrosion and electrochemical study occurs with materials in contact with sea water. A galvanic series of materials in equine blood gives possible electrode pairings for the cathode and anode, although not intended to be an exhaustive list of electrode pairings applicable to the invention.

Listing of Electrode Pairings (Electrode Potentials Measured in Equine Blood)

| Cathode (potential) | Anode (potential) |
|---|---|
| Titanium (3.5 V) | Tantalum (1.65 V) |
| | Platinum (1.45 V) |
| | Palladium (1.35 V) |
| | Iridium (1.15 V) |
| | Gold (1.0 V) |
| | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Tantalum (1.65 V) | Platinum (1.45 V) |
| | Palladium (1.35 V) |
| | Iridium (1.15 V) |
| | Gold (1.0 V) |
| | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Platinum (1.45 V) | Palladium (1.35 V) |
| | Iridium (1.15 V) |
| | Gold (1.0 V) |
| | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Palladium (1.35 V) | Iridium (1.15 V) |
| | Gold (1.0 V) |
| | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Iridium (1.15 V) | Gold (1.0 V) |
| | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Gold (1.0 V) | Chromium (0.75 V) |
| | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Chromium (0.75 V) | 316SS (0.48 V) |
| | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| 316SS (0.48 V) | Zirconium (0.32 V) |
| | Tungsten (0.12 V) |
| | Aluminum-Magnesium Alloy (−0.65 V) |
| | Zinc (−0.95 V) |
| | Magnesium (−1.55 V) |
| Zirconium (0.32 V) | Tungsten (0.12 V) |
| | Aluminum-Magnesium Alloy (−0.65 V) |
| | Zinc (−0.95 V) |
| | Magnesium (−1.55 V) |
| Tungsten (0.12 V) | Aluminum-Magnesium Alloy (−0.65 V) |
| | Zinc (−0.95 V) |
| | Magnesium (−1.55 V) |
| Aluminum-Magnesium Alloy (−0.65 V) | Zinc (−0.95 V) |
| | Magnesium (−1.55 V) |
| Zinc (−0.95 V) | Magnesium (−1.55 V) |

In each of the listed pairings of electrode, one material is most/more noble such as titanium is selected for the cathode and a least/less noble material is such as magnesium is selected for the anode. The galvanic series as measured in equine blood gives a reference for the electrode potential. In the example of a titanium cathode and magnesium anode, the difference in potential between these materials (titanium at 3.5V and magnesium at −1.55V) yields 5.05V which would be utilized in feedback circuit 140. The potential difference between the electrodes is due to oxidation-reduction reaction occurring between the electrodes and the environment which in this example is blood. The current generated by the electrochemical reaction is in proportion to the surface area of the reacting electrodes where larger surfaces areas generate larger currents. The feedback circuit 140 will be powered by the electric potential resulting from the selection of electrode pairings and the electrical current resulting from the selection of electrode area. The power of the resulting circuit can then be targeted by selection of electrode materials and electrode area as is known by one of ordinary skill in the art.

Depending on the materials chosen for first and second electrodes 132, 136, some galvanic corrosion or degradation of anode 132 may occur. However, as stent delivery and apposition detecting system 100 is only temporarily implanted within the patient, such corrosion of anode 132 would not be total or complete. Further, as the material of anode 132 is biocompatible, such corrosion would not be harmful to the patient.

The electrochemical cell potential may be tailored or manipulated due to the characteristic electrode potentials of the individual electrodes when in contact with a specific electrolyte or environment, i.e., tissue or blood. While a first distinct pairing of electrodes in contact with blood may result in an electrochemical cell having a relatively low cell potential, a second distinct pairing of electrodes in contact with blood may result in an electrochemical cell having a relatively high cell potential. Further, the distinct pairings of electrodes uniquely interact with a specific electrolyte under non-standard conditions such as within the body. Accordingly, in one embodiment, a dissimilar metal pairing for first and second electrodes 132, 136 is selected to give the resulting electrochemical cell a low cell potential when exposed to blood and a higher cell potential when exposed to tissue. In another embodiment, a dissimilar metal pairing for the electrode pairing 132, 136 is selected to give the resulting electrochemical cell a low cell potential when exposed to tissue and a higher cell potential when exposed to blood.

In order to transmit the current generated by the electrochemical cell created with first and second electrodes 132, 136 through the length of balloon catheter 102 to a feedback circuit 140, an electrically conductive lead 134 extends along outer shaft 104 between electrode 132 and feedback circuit 140. Similarly, an electrically conductive lead 138 extends along outer shaft 104 between electrode 136 and feedback circuit 140. Leads 134, 138 may be wires or insulated wires. Feedback circuit 140 in conjunction with leads 134, 138 and first and second electrodes 132, 136 form a complete electrical circuit that includes a portion of a patient's body extending between first and second electrodes 132, 136. First and second electrodes 132, 136 are fixedly attached to the distal ends of leads 134, 138, respectively, by any suitable means so long as electrodes 132, 136 are in electrical communication with leads 134, 138. For example, the electrodes may be attached via welding, soldering, by the use of an electrically conductive adhesive, or by another mechanical method.

As shown in FIG. 1, leads 134, 138 may run along the outside of shaft 104 in a longitudinal manner and be secured into place via tape, adhesive, shrink fit tubing, or another mechanical method. In one embodiment, leads 134, 138 may be wrapped in a helical manner around the outside of shaft 104 and be secured into place. In another embodiment hereof, leads 134, 138 may run within a lumen, i.e., inflation lumen 114 or guidewire lumen 118, of balloon catheter 102 so long as the presence of the lead does not interfere with the operation of the lumen. In yet another embodiment, leads 134, 138 may extend within the sidewall of shaft 104 and form a reinforcement member of the catheter shaft to add strength thereto.

Feedback circuit 140 is located outside of the patient at the proximal end of stent delivery and apposition detecting system 100, and generates an alert to notify the user when the electric potential of the electrochemical cell indicates that first and second electrodes 132, 136 are in contact with tissue of the vessel wall. In one embodiment, feedback circuit 140 is a light emitting diode (LED) circuit, The LED is designed or tailored to illuminate when the electric potential or voltage of the electrochemical cell is greater than a given threshold value. The threshold value is selected to distinguish between when first and second electrodes 132, 136 are in contact with blood and when first and second electrodes 132, 136 are in contact with tissue of the vessel wall. For example, stent delivery and apposition detecting system 100 may be designed such that the voltage generated by the electrochemical cell when first and second electrodes 132, 133 are in contact with blood may be in the range of 3-5 volts, and the voltage generated by the electrochemical cell when first and second electrodes 132, 136 are in contact with tissue of the vessel wall may be in the range of 0.5-2 volts. In one embodiment, the LED circuit may be selected or designed to illuminate at a threshold value of 3 volts. Thus, once first and second electrodes 132, 136 are in contact with the vessel wall and the voltage generated by the electrochemical cell is less than the threshold value of 3 volts, the LED circuit of feedback circuit 140 illuminates to alert the user that the stent is fully deployed in apposition with the vessel wall. In another embodiment, the LED circuit may be designed to illuminate for a specific range of values such as 0.5-2 volts. Thus, while first and second electrodes 132, 136 are in contact with the vessel wall and the voltage generated by the electrochemical cell is within 0.5-2 volts, the LED circuit of feedback circuit 140 illuminates to alert the user that the stent is fully deployed into apposition with the vessel wall.

Feedback circuit 140 may be self-powered meaning that the current and voltage generated by the electrochemical cell is sufficient to illuminate the LED circuit. In the self-powered embodiment, no external power source is required for the operation of stent delivery and apposition detecting system 100. Rather, the cell potential or voltage of the electrochemical cell formed by first and second electrodes 132, 136, the size of the electrodes, and the environmental electrolyte is utilized to power feedback circuit 140. Although LED circuits may be designed to illuminate with very small potentials which makes them a good candidate for the self-powered embodiment, other self-powered feedback mechanisms are possible. For example, feedback circuit 140 may include an auditory or tactile, i.e., vibrations, alert to alert the user of complete stent apposition as long as the feedback circuit may operate on the relatively small power generated by first and second electrodes 132, 136.

Although balloon catheter 102 is described herein as an over-the-wire catheter in which the guidewire shaft extends the entire length of the catheter, it would be understood by one of ordinary skill in the art that stent delivery and apposition detecting system 100 may include any type of catheter known in the art, including a rapid-exchange catheter in which the guidewire shaft extends only within the distal portion of the catheter, a core wire catheter, and any other appropriate balloon catheters. For example, conventional balloon catheters such as those shown or described in U.S. Pat. Nos. 6,736,827 to McAndrew et al.; 6,554,795 to Bagaoisan et al.; 6,500,147 to Omaleki et al.; and 5,458,639 to Tsukashima et al., each of which is incorporated by reference herein in its entirety, may be used in conjunction with the stent delivery and apposition detecting system described herein.

Balloon catheter 102 may have any suitable working length, for example, 50 cm-200 cm, suitable to extend to a target location within the vasculature. Shafts 104, 106 can be of any suitable construction and made of any suitable material, such as an extruded shaft formed of any suitable flexible polymeric material. Non-exhaustive examples of polymeric materials for shafts 104, 106 are polyethylene, PEBA, polyamide, HDPE, PEBAX, polyethylene terephalate (PET), nylon, silicone, LDPE, HMWPE, polyurethane, or combinations of any of these, either blended or co-extruded. Optionally, outer shaft 106 or some portion thereof may be formed as a composite having a reinforcement material incorporated within a polymeric body in order to enhance strength, flexibility, and/or toughness. Suitable reinforcement layers include braiding, wire mesh layers, embedded axial wires, embedded helical or circumferential wires, and the like. In one embodiment, the reinforcement material may be or include lead 134 and/or lead 138. In an embodiment, the proximal portion of the catheter may in some instances be formed from a reinforced polymeric tube, for example, as shown and described in U.S. Pat. No. 5,827,242 to Follmer et al., which is incorporated by reference herein in its entirety.

In one embodiment hereof, at least a portion of stent 130 may be coated with a therapeutic agent (not shown). Stent 130 may be coated with a controlled-release polymer and/or drug, as known in the art, for reducing the probability of undesired side effects, e.g., restenosis. The therapeutic agent can be of the type that dissolves plaque material forming the stenosis or can be an antineoplastic agent, an antiproliferative agent, an antibiotic, an antithrombogenic agent, an anticoagulant, an antiplatelet agent, an anti-inflammatory agent, combinations of the above, and the like. Such drugs can include TPA, heparin, urokinase, zotarolimus or sirolimus, for example. Of course stent 130 can be used for delivering any suitable medications to the walls of a body vessel.

Referring now to FIG. 2, another embodiment hereof is shown in which a balloon 208 has two sets of electrode pairs mounted thereon for detecting when a stent (removed from FIG. 2 for clarity) achieves proper wall apposition during deployment. A first set of electrodes, first anode 232A and first cathode 236A, are dissimilar metals that create a first electrochemical or galvanic cell in conjunction with an electrolyte from the environment surrounding balloon 208, i.e., blood or tissue. Similarly, a second set of electrodes, second anode 232B and second cathode 236B, are dissimilar metals that create a second electrochemical or galvanic cell in conjunction with an electrolyte from the environment surrounding balloon 208, i.e., blood or tissue. The first set of electrodes 232A, 236A are longitudinally spaced apart from each other in that electrode first 232A is mounted onto a proximal portion 224 of balloon 208 and first electrode 236A is mounted onto a distal portion 228 of balloon 208. The second set of electrodes 232B, 236B are spaced approximately one hundred eighty degrees apart from the first set of electrodes 232A, 236A such that the electrode sets are positioned at two opposing locations around the circumference of balloon 208. The second set of electrodes 232B, 236B are longitudinally spaced apart from each other in that electrode second 232B is mounted onto proximal portion 224 of balloon 208 and second electrode 236B is mounted onto distal portion 228 of balloon 208. Increasing the number of electrode pairs allows the stent delivery and apposition detecting system to detect vessel wall contact at more locations along the contact area of balloon 208, thereby increasing the sensitivity and accuracy of detecting complete or full stent apposition against the vessel wall. As will be apparent to one of ordinary skill in the art, the number of sets of electrode pairs and their longitudinal and radial spacing may be varied to suit a particular application. For example, in one embodiment (not shown), three sets of electrode pairs may be spaced approximately one hundred twenty degrees apart such that electrode pairs are positioned at three locations around the circumference of balloon 208. In another embodiment (not shown), four sets of electrode pairs may be spaced approximately ninety degrees apart such that they are positioned at four locations around the circumference of balloon 208. In addition, referring now to FIG. 3, a third set of electrodes 332C, 336C is positioned on an intermediate portion 226 of balloon 208 such that the electrode pairs are positioned at different longitudinal locations along the length of balloon 208. The third set of electrodes 332C, 336C are dissimilar metals that create a third electrochemical or galvanic cell in conjunction with an electrolyte from the environment surrounding balloon 208, i.e., blood or tissue. The third set of electrodes 332C, 336C are spaced approximately one hundred eighty degrees apart such that they are positioned at two opposing locations around the circumference of balloon 208.

When multiple sets of electrode pairs are utilized for detecting when a stent achieves proper wall apposition during deployment, each set may have a separate feedback circuit. For example, as shown in FIG. 2, first set of electrodes 232A, 236A transmit the current generated between electrodes 232A, 236A to a feedback circuit 240A via electrically conductive leads 234A, 238A, respectively. Feedback circuit 240A in conjunction with leads 234A, 238A and electrodes 232A, 236A form a complete electrical circuit that includes a portion of a patient's body extending between electrodes 232A, 236A. Feedback circuit 240A generates an alert to notify the user when the electric potential of the first electrochemical cell indicates that electrodes 232A, 236A are in contact with tissue of the vessel wall. Similarly, second set of electrodes 232B, 236B transmit the current generated between electrodes 232B, 236B to a feedback circuit 240B via electrically conductive leads 234B, 238B, respectively. Feedback circuit 240B in conjunction with leads 234B, 238B and electrodes 232B, 236B form a complete electrical circuit that includes a portion of a patient's body extending between electrodes 232B, 236B. Feedback circuit 240B generates an alert to notify the user when the voltage generated by the second electrochemical cell indicates that electrodes 232B, 236B are in contact with tissue of the vessel wall. The use of multiple feedback circuits allows the user to separately monitor when different portions of balloon 208 are pressed against the vessel wall. Alternatively, as shown in FIG. 3, when multiple sets of electrode pairs are utilized for detecting when a stent achieves proper wall apposition during deployment, the stent delivery and apposition detecting system may utilize only one feedback circuit 340 that generates an alert to signal when all electrode pairs are in contact with the vessel wall. Feedback circuit 340 may be tailored or designed to illuminate above a threshold value or within a range that reflects when the voltage generated from all the three electrochemical cells, collectively, indicates that the stent is fully deployed in apposition with the vessel wall.

When the stent delivery and apposition detecting system includes multiple sets of electrode pairs for detecting proper stent apposition, it is important to ensure that individual and separate electrochemical cells are formed by the correct electrode pair. In one embodiment, in order to ensure that the correct electrode pair matches up to form an electrochemical cell. each electrode pair has a unique pairings of metals. For example, in the embodiment of FIG. 2 which has two sets of electrode pairs, the first set of electrodes 232A, 236A may have a Platinum-Magnesium pairing of metals that has a predicted cell potential or voltage of 4 volts when in contact with blood and the second set of electrodes 232B, 236B may have a Platinum-Zinc pairing of metals that has a predicted cell potential or voltage of 2.35 volts when in contact with blood, As the stent is deployed, the environment of the electrode will change from blood to tissue, which also affects the cell potential. The feedback circuit 240A can be designed to alert the user when the stent is fully deployed in apposition with the vessel wall by signaling when the circuit is no longer at 4 volts, corresponding to the predicted cell potential or voltage of the first set of electrodes 232A, 236A in blood or by signaling when the cell potential of electrodes 232A, 236A achieve the specific voltage for tissue contact. Similarly, feedback circuit 240B can be designed to alert the user that the stent is fully deployed in apposition with the vessel wall by signaling when the circuit is no longer at 2.35 volts, corresponding to the predicted cell potential or voltage of the second set of electrodes 232B, 236B in blood or by signaling when the cell potential of electrodes 232A, 236A achieve the specific voltage for tissue contact. Since the feedback circuits only respond to the predicted cell potentials of the corresponding unique electrode pair, the stent delivery and apposition detecting system detects when the particular intended electrode pair or match has contacted the tissue of the vessel wall. In another embodiment (not shown), an externally powered computing device may be attached to the feedback circuit(s) and an algorithm programmed into the computing device discriminates when the particular intended electrode pairing has contacted the vessel wall.

In another embodiment hereof, the feedback circuit may be powered by an external power source rather than by the cell potential of the electrochemical cell. For example, FIG. 4 is a schematic illustration of an externally powered circuit for use in a stent delivery and apposition detecting system in accordance with an embodiment hereof. The complete circuit includes a first electrode 432, a second electrode 436, a portion of a patient's body extending between electrodes 432, 436, and a processor 452 for connection to the first and second electrodes 432, 436. In an embodiment, processor 452 includes an amplifying circuit and/or an electrochemical potential arithmetic operation section having logic resources, such as a microprocessor and/or memory resources configured to analyze, store, and/or display electrochemical potential information derived from electrodes 432, 436. The electric potential measurement of the electrochemical cell undergoes analysis and/or further processing via processor 452 such that the stent delivery and apposition detecting system may discriminate between different types of matter, i.e., blood, tissue, thrombus, calcified lesion, air pockets, etc., with increased sensitivity. An external power source 450 powers processor 452. Power source 450 and processor 452 are connected together externally or they may be combined in an integral device. A feedback circuit 440 is connected to processor 452. Electrically conductive leads 434, 438 extend along the length of the stent delivery and apposition detecting system and communicate with electrodes 432, 436, respectively. The proximal ends of leads 434, 438 extend outside of the body to be electrically connected with processor 452.

An alert is generated by feedback circuit 440 when the stent has achieved proper wall apposition with tissue of the vessel wall. Since the circuit of FIG. 4 is externally powered, feedback circuit 440 is not required to have a low-power operating status. Rather, feedback circuit 440 may include one or more types of alerts including visual, auditory, and tactile, i.e., vibration, alerts. In one embodiment, feedback circuit 440 may produce a visual display or readout of the measured/calculated electric potential values.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent delivery and apposition detecting system comprising:
    a balloon catheter having a balloon mounted at the distal end thereof with a stent coupled to an intermediate portion of the balloon; and
    at least one electrode pair including a first electrode and a second electrode of dissimilar metals mounted on the balloon such that the first electrode is mounted proximal to the stent and the second electrode is mounted distal to the stent, wherein the stent delivery and apposition detecting system uses an electrochemical cell created by the electrode pair to detect when the stent achieves apposition with a vessel wall during deployment.

2. The stent delivery and apposition detecting system of claim 1, further comprising:
    a feedback circuit electrically connected to the at least one electrode pair, wherein the feedback circuit generates an alert for a user when an electric potential of the electrochemical cell indicates that the electrode pair is in contact with tissue of the vessel wall.

3. The stent delivery and apposition detecting system of claim 2, wherein the feedback circuit is designed to generate the alert when the electric potential of the electrochemical cell is less than a given threshold value selected to distinguish between when the electrode pair is in contact with blood and when the electrode pair is in contact with tissue of the vessel wall.

4. The stent delivery and apposition detecting system of claim 3, wherein the feedback circuit is powered by the electric potential of the electrochemical cell created.

5. The stent delivery and apposition detecting system of claim 4, wherein the feedback circuit is a light emitting diode (LED) circuit.

6. The stent delivery and apposition detecting system of claim 2, wherein the feedback circuit is powered by an external power source.

7. The stent delivery and apposition detecting system of claim 6, wherein the feedback circuit generates a visual, auditory, or tactile alert.

8. The stent delivery and apposition detecting system of claim 6, further comprising:
    a processor that amplifies and processes the electric potential of the electrochemical cell.

9. The stent delivery and apposition detecting system of claim 2, further comprising:
    a first conductive lead extending between the first electrode of the at least one electrode pair and the feedback circuit, and a second conductive lead extending between the second electrode of the at least one electrode pair and the feedback circuit.

10. The stent delivery and apposition detecting system of claim 9, wherein the first and second conductive leads extend along an outside surface of the balloon catheter.

11. The stent delivery and apposition detecting system of claim 9, wherein the first and second conductive leads extend within a lumen of the balloon catheter.

12. The stent delivery and apposition detecting system of claim 1, wherein the first electrode is mounted on a first side of the balloon and the second electrode is positioned on a second opposing side of the balloon from the first electrode.

13. The stent delivery and apposition detecting system of claim 1, wherein the first electrode of the at least one electrode pair is formed from a material selected from the group consisting of magnesium and zinc and the second electrode of the at least one electrode pair is formed from a material selected from the group consisting of platinum and gold.

14. The stent delivery and apposition detecting system of claim 1, wherein multiple sets of electrode pairs are mounted around the circumference of the balloon.

15. The stent delivery and apposition detecting system of claim 1, wherein the electrochemical cell uses an oxidation-reduction chemical reaction to generate an electric current.

16. The stent delivery and apposition detecting system of claim 1, wherein the electrochemical cell includes an electrolyte from the environment surrounding the balloon.

17. The stent delivery and apposition detecting system of claim 16, wherein the difference between individual potentials of the first and second electrodes of the electrode pair is with respect to the electrolyte.

18. The stent delivery and apposition detecting system of claim 16, wherein the electrochemical cell potential is configured to change as the balloon is inflated or deflated.

19. A method of deploying a stent at a target site within a vessel, the method comprising the steps of:
   transluminally positioning a balloon catheter at the target site within the vessel, wherein the balloon catheter includes a balloon at the distal end thereof with the stent coupled to an intermediate portion of the balloon; and at least one electrode pair including a first electrode and a second electrode of dissimilar metals mounted on the balloon such that the first electrode is mounted proximal to the stent and the second electrode is mounted distal to the stent; and
   radially expanding the balloon until the stent achieves apposition with a wall of the vessel, wherein an electrochemical cell created by the electrode pair is used to detect when the stent achieves apposition with the wall of the vessel.

20. The method of claim 19, wherein a feedback circuit is electrically connected to the at least one electrode pair such that the feedback circuit generates an alert for a user when an electric potential of the electrochemical cell indicates that the electrode pair is in contact with tissue of the vessel wall.

21. The method of claim 20, wherein the feedback circuit is designed to generate the alert when the electric potential of the electrochemical cell is less than a given threshold value selected to distinguish between when the electrode pair is in contact with blood and when the electrode pair is in contact with tissue of the vessel wall.

22. The method of claim 21, wherein the feedback circuit is powered by the electrochemical cell created by the electrode pair.

23. The method of claim 19, wherein multiple sets of electrode pairs are mounted around the circumference of the balloon.

* * * * *